(12) United States Patent
Kuth et al.

(10) Patent No.: US 7,792,567 B2
(45) Date of Patent: Sep. 7, 2010

(54) METHOD AND SYSTEM FOR CORRELATING ACQUISITION OF IMAGES OF A MOVING ORGAN WITH THE MOVEMENT OF THE MOVING ORGAN

(75) Inventors: Rainer Kuth, Herzogenaurach (DE); Axel Schreiber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1276 days.

(21) Appl. No.: 11/230,417

(22) Filed: Sep. 20, 2005

(65) Prior Publication Data

US 2006/0079790 A1 Apr. 13, 2006

(30) Foreign Application Priority Data

Sep. 20, 2004 (DE) .................. 10 2004 045 495

(51) Int. Cl.
*A61B 5/05* (2006.01)
(52) U.S. Cl. .................. 600/413; 600/421; 600/428
(58) Field of Classification Search .................. 600/410, 600/411, 413, 419, 421, 424, 425, 427, 428, 600/508; 382/128, 130, 131; 359/227, 230; 348/65, 77
See application file for complete search history.

(56) References Cited

U.S. PATENT DOCUMENTS

| | | | |
|---|---|---|---|
| 4,694,837 A | 9/1987 | Blakeley et al. | |
| 5,088,501 A | 2/1992 | Niewisch | |
| 5,997,883 A * | 12/1999 | Epstein et al. | 324/306 |
| 6,771,999 B2 * | 8/2004 | Salla et al. | 600/413 |
| 2004/0111025 A1 | 6/2004 | Avniash et al. | |
| 2005/0113672 A1 * | 5/2005 | Salla et al. | 600/413 |

FOREIGN PATENT DOCUMENTS

| | | |
|---|---|---|
| DE | 195 04 758 | 8/1996 |
| GB | 2 161 937 | 1/1986 |
| WO | WO 03096894 A1 * | 11/2003 |

OTHER PUBLICATIONS

Raza et al. Optical instrumentation for respiration measurement in magnetic resonance scanners. IEEE Colloquium on Progress in Fibre Optic Sensors and Their Applications. 15: p. 1-5. Nov. 7, 1995.*
"Optical Instrumentation For Respiration Measurement in Magnetic Resonance Scanners," Raza et al, IEEE Colloquium On Progress in Fibre Optics Centers and their Applications, Nov. 7, 1995, pp. 15/1-15/5.
"An Optical 6-axis Force Sensor for Brain Function Analysis Using fMRI," Takahashi et al, Sensors 2003, Proceedings of IEEE, vol. 1, Oct. 22-24, 2003, pp. 253-258.
"Fiber Optic Sensors For Biomedical Measurements In Magnetic Resonance Imaging (MRI)", Shen et al, 39th Electronic Components Conference, May 1989, pp. 479-481.

* cited by examiner

*Primary Examiner*—Brian Casler
*Assistant Examiner*—Parikha S Mehta
(74) *Attorney, Agent, or Firm*—Schiff Hardin LLP

(57) ABSTRACT

In a method, sensor and system for producing time-limited images of a moving organ of a human or animal body, an imaging apparatus acquires image data and, using a sensor situated outside the body, a signal is registered that represents the movement of the organ that is to be imaged. The image data acquisition is coordinated with this signal. A fiber optic sensor is used as the sensor.

16 Claims, 2 Drawing Sheets

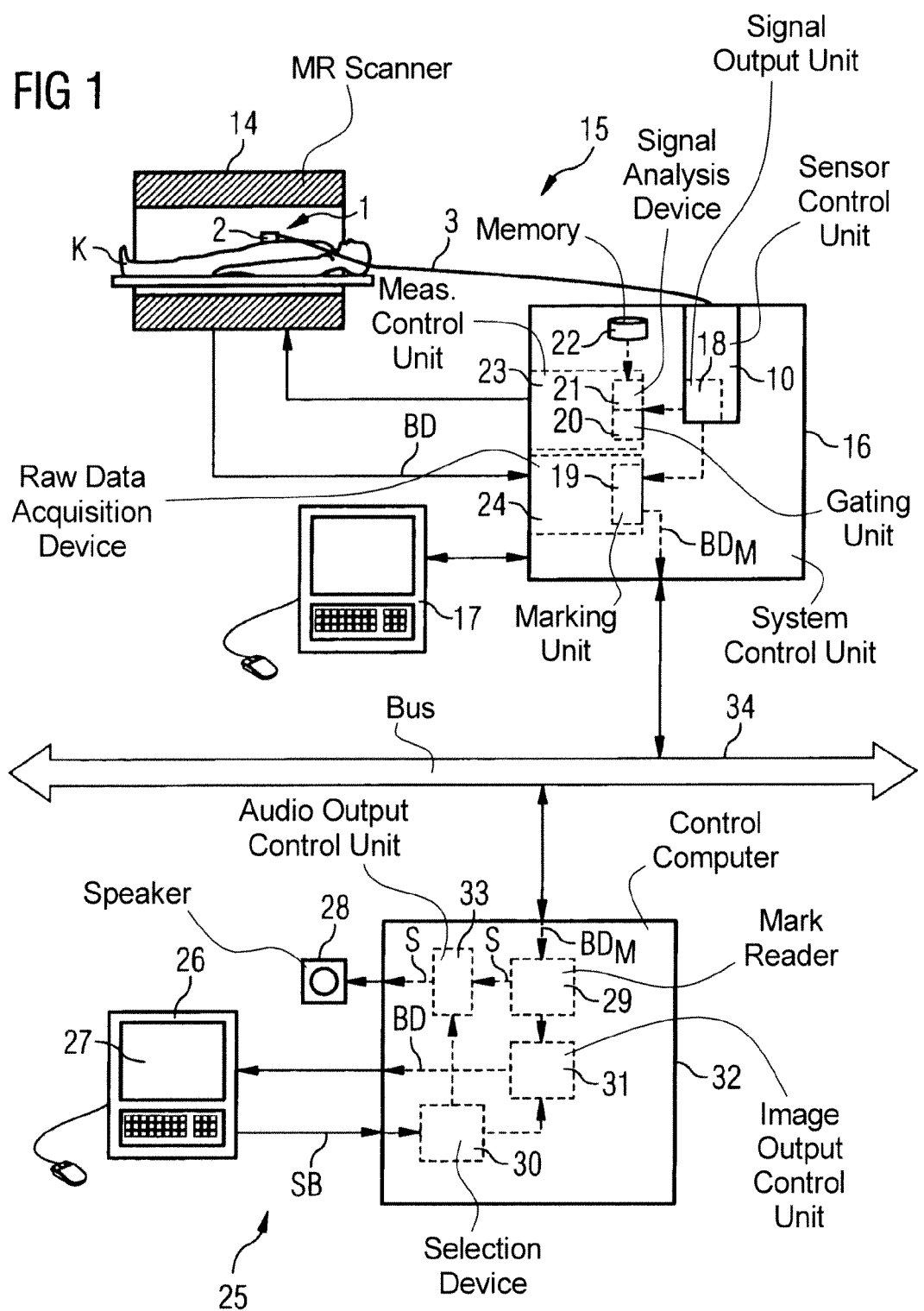

METHOD AND SYSTEM FOR CORRELATING ACQUISITION OF IMAGES OF A MOVING ORGAN WITH THE MOVEMENT OF THE MOVING ORGAN

BACKGROUND OF THE INVENTION

1. Field of the Invention

The present invention concerns a method for producing a time-limited image of a moving organ of a human or animal body, such as for imaging a beating heart, of the type wherein image data are acquired using an imaging apparatus, wherein using a sensor situated outside the body, a signal is registered that represents the movement of the organ that is to be imaged, and wherein the image data acquisition is coordinated with this signal. The present invention also concerns a sensor for use in such a method, as well as a system, having such a sensor, for producing time-limited image of a moving organ of a human or animal body. The present invention also concerns a method and a device for displaying images obtained using such a method.

2. Description of the Prior Art

In modern medicine, many types of imaging modalities are known, the basic goal of which is to obtain comprehensive knowledge of a particular organ and its state without having to surgically open the body. Typical medical imaging systems include, for example, magnetic resonance systems, computed tomography systems, x-ray systems, and ultrasound systems. Such medical imaging systems are used, for example to obtain images of bone structure, the brain, the heart, the lungs, the gastrointestinal region, etc. When recording images of an organ that moves, for example cardiological images, images of the lungs, or images of the peristaltic action of the small intestine or the swallowing process of the esophagus, it is often desirable to produce an image at a particular point in time (static image) or within a particular time period of the movement, in order to observe the behavior of the organ precisely at this point in time or during this particular time period.

One known method for this purpose is gating. In this method in the case of cardiological imaging as an example, an ECG signal is recorded. From the ECG, a particular significant event, for example the occurrence of the R-peak of the ECG, is used as a trigger signal for making an exposure at a precisely determined point in the movement of the heart. A problem with triggering with the aid of an ECG is that for this purpose a number of electrodes must be attached directly to the body. These electrodes are electrically conductive sensors, generally made of metal, which can cause disturbances in the recorded images. In addition, it takes a certain amount of time to attach all the required electrodes to the skin of the person or animal being examined. While the patient or animal is being connected to the ECG apparatus, the imaging system generally cannot be used for other purposes. This additional waiting period, taking place for a large number of examinations, unnecessarily reduces the active use of the relatively expensive imaging systems, and thus increases the costs of an individual examination.

In order to solve the problem of the sensor causing disturbances in the recorded images of the organ, in U.S. Published Application 2004/0111025, it is proposed to situate a suitable sensor outside the measurement space of the imaging system and to connect the sensor to the patient via a patient-sensor interface. In the publication, the use of a liquid-filled non-metallic conductor tube in combination with a mechanical sensor is described, for example an acceleration sensor, that reacts to non-electrical events in the body, such as breathing. The patient-side of the patient-sensor interface must be secured on the thorax of the patient. Movement due to the patient's breathing is then communicated to the sensor via the liquid-filled conductor tube. There the signal is picked-up by the sensor. The signal obtained with this additional sensor is then used to control the image data acquisition such that images of the organ, in particular states of movement, are produced. As long as the sensor does not interfere with the imaging, the acceleration sensor can be positioned directly on the patient. In imaging modalities in which this would result in a superimposition of the sensor in the imaging exposures, the patient-sensor interface must be intermediately coupled, which is relatively difficult. For this reason, using this method it is not possible to rapidly prepare the patient for an examination by the imaging system.

SUMMARY OF THE INVENTION

An object of the present invention is to provide a user-friendly and time-saving method for producing and displaying images of an organ of the human or animal body, as well as corresponding devices and systems for carrying out such a method.

This object is achieved in accordance with the invention by a method for producing images of an organ of the human or animal body in which an imaging apparatus is used to acquire image data, and wherein a sensor situated outside the body is used to register a signal that represents a movement of the organ to be imaged, and wherein the image data acquisition is coordinated with this signal, with a fiber optic sensor being used as the sensor.

According to the present invention, such a fiber optic sensor for use in the method according to the present invention has a light waveguide system with a supply conductor and a return conductor, as well as a coupling device that couples light from the supply conductor into the return conductor, the light waveguide system and/or the coupling device being situated and/or fashioned such that the portion of coupled light depends on an external force acting on the fiber optic sensor.

This external force, for example, can be an acceleration force, a pressure force, or the like. Thus, depending on where and how the sensor is positioned, this sensor can detect various events in the body, for example breathing, the heartbeat, or a pulse. In contrast to the known method described in the prior art cited above, here the fiber optic sensor itself can be situated directly on the body, i.e., without a patient-sensor interface. In the simplest case, the fiber optic sensor need merely be placed on the thorax of the patient in order to record, for example, a signal for the breathing or the heartbeat, in such a way that actual skin contact is not required. Thus, it is not necessary for the patient to disrobe partially in order to attach the sensor. The preparation of the patient for an image exposure therefore can take place considerably faster than with the method described above.

A corresponding system for imaging an organ of the human or animal body has an imaging apparatus, for example a magnetic resonance apparatus, a computer tomography apparatus, an ultrasound apparatus, or an x-ray apparatus. In addition, this system has a fiber optic sensor according to the present invention, as cited above, for the registration of a signal representing a movement of the organ that is to be imaged. Finally, the system has a signal combining device in order to coordinate the image data acquisition with this signal.

For coordinating the signal representing the state of movement of the organ that is to be imaged with the acquired image data, a wide variety of possibilities exists.

As mentioned above, one version is known as gating, in which the image data acquisition is controlled or triggered by the signal recorded by the sensor. Thus, for example it can be ensured that image data are always acquired at particular phase points in a cyclical movement. Here, data can be acquired over a larger number of phases, in order to later produce a particularly good high-resolution image therefrom. For this purpose, a corresponding system according to the present invention has a gating unit that controls the image data acquisition on the basis of the signal acquired using the sensor. This gating unit also can be integrated, for example, as a part of the signal combining device, into a measurement control unit of the imaging apparatus—preferably in the form of a software program.

Another possibility is to mark the acquired image data for combining with the signal recorded by the sensor. Here, the acquired image data can be marked immediately dependent on the signal recorded by the sensor, for example by integrating each of the signal values themselves, occurring at a particular exposure time, into the image data sets in coded fashion, in a defined manner. Alternatively or additionally, it is possible to provide the acquired image data with time markers on the basis of a time scale correlated with the signal.

For this purpose, a corresponding system according to the present invention has a marking unit that marks the acquired image data for combination with the signal acquired by the sensor. Such a marking unit can be, for example a signal combination device, or can be integrated in an image data acquisition/evaluation device, again preferably in the form of software.

As used herein, "acquired image data" means not only the originally-acquired raw image data, but also, if applicable, the images already obtained therefrom that are to be displayed. That is, a marking of the image data can take place in such a way that the acquired raw image data and/or the images obtained therefrom that are to be displayed are provided with suitable markings. Here it is essential only that the correlation be maintained between the image data and the signal representing the movement of the organ being imaged.

To the extent that the image data acquired by the imaging measurement device have been marked for combination with the signal obtained in the image data acquisition, in a suitable method for displaying the images obtained using this method it can be ensured that, when displaying a sequence of images, the signal representing the movement of the organ being imaged is emitted acoustically and/or optically in a chronologically correlated fashion. That is, the recorded signal for example the heartbeat, is acoustically emitted synchronously with the representation of the measured image data.

A corresponding apparatus according to the present invention for displaying the images obtained using the method described above has a mark reader that reads the markings present in the image data for combining with the signal, obtained in the image data acquisition, that represents the movement of the organ that is to be imaged. In addition, the apparatus has a display unit for the representation of the images, and a signal output unit that, during the reproduction of a sequence of images, emits the corresponding signal acoustically, e.g. using a speaker, and/or optically, for example on the display unit on which the images are shown, in a chronologically correlated fashion.

A significant advantage of a synchronous output of the additionally recorded signals with the associated image sequence is that this allows particular pathologies to be found more rapidly. This is because, in some circumstances, certain pathologies of an organ that moves cyclically (periodically) only sporadically exhibit movement patterns that deviate from the normal pattern. If, synchronized with the representation of the radiological images, audio signals representing the movement of the organ are reproduced, for example the sound of a heartbeat in cardiological exposures, the physician operating apparatus can recognize anomalies better and faster by listening to the signal simultaneously with his or her viewing of the image sequence. Preferably, the operator can vary the output speed of the sound and the image in synchronous fashion.

Preferably, the display unit has a selection device with a user interface, or has a connection to the general user interface of the apparatus. The operator can then select a time segment, for example with the aid of the signal, representing the movement of the organ being imaged. Subsequently, a sequence of images recorded in the relevant time segment is reproduced, preferably synchronized with the newly emitted signal. Moreover, for the selection of a time segment, it is possible for the operator to separately emit acoustically, ahead of time and at a higher speed, the signal representing the movement of the organ being imaged, without displaying the parallel images at the same time. The sound and images of the time segment are not reproduced together until a corresponding time segment has been selected.

In a preferred embodiment, in what is called "cine-loop mode" it is possible to reproduce a selected sequence of images repeatedly one after the other, e.g. until an endless loop is terminated. In this way, a pathological event that occurs only sporadically can be better analyzed.

In a preferred embodiment, using the signal recorded by the sensor, possible anomalies in the movement of the organ are automatically detected. The image data acquired during the occurrence of a possible anomaly can then be separately marked, and/or the image data acquisition can be started dependent on the occurrence of a possible anomaly. That is, the image data acquisition is triggered by the occurrence of a possible (suspected) anomaly.

The detection of possible anomalies can occur, for example, by a comparison of a sequence of signals acquired by the sensor with a sample signal sequence. Here, it is possible for a sample signal sequence of a cyclical movement of an organ to be obtained, preferably, on the basis of at least one previous signal sequence. Thus, a simple comparison with a preceding sequence can take place, or from a series of preceding sequences an average value sequence or the like can be formed can be used as a sample signal sequence.

In a preferred exemplary embodiment of the fiber optic sensor, the coupling device has a reflector element that reflects light radiated from the supply conductor into the return conductor.

The portion of the light that is coupled can be made dependent on the external force acting on the fiber optic sensor in relatively simple fashion by providing the coupling device with a balance weight, mounted in movable fashion, that is coupled with the reflector device in such a way that the portion of light radiated from the supply conductor that is reflected into the return conductor by the reflector device depends on the position of the balance height. The balance weight, for example, be held flexibly in a rest position in which a precisely defined light portion is coupled. As soon as an accelerating force acts on the sensor, the balance weight is moved out of the rest position by its inertia, thus ensuring a corresponding change in the portion of light that is coupled.

Alternatively, the reflector device can be coupled with a membrane such that when there is a change in a acoustic pressure acting on the membrane, the portion of the light radiated from the supply conductor that is reflected into the return conductor by the reflector device changes correspondingly.

DESCRIPTION OF THE DRAWINGS

FIG. 1 schematically illustrates an exemplary embodiment of a system according to the present invention for imaging an organ, having a fiber optic sensor according to the present invention and having a display device according to the present invention.

DESCRIPTION OF THE PREFERRED EMBODIMENTS

Figure 2A:
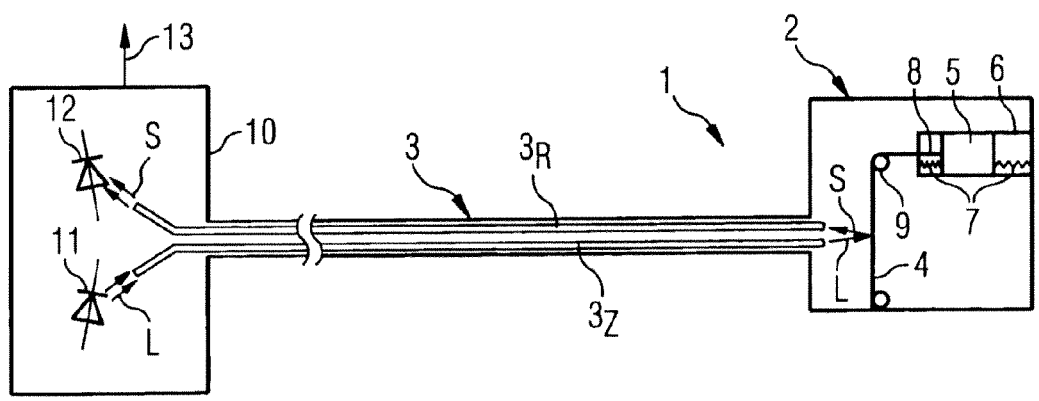
FIG. 2a schematically illustrates the functioning of an exemplary embodiment of a fiber optic sensor according to the present invention, without the action of an external force on the sensor.

In the exemplary embodiment shown in FIG. 1 of a system according to the present invention for imaging an organ of a human or animal body K, the system is a magnetic resonance system 15.

The core of this system 15 is a magnetic resonance (MR) scanner 14 in which the body K of a patient being examined is positioned on a bed in an annular basic field magnet. Inside the basic field magnet, there is conventionally situated a radio-frequency antenna (not shown) for emitting radio-frequency pulses. Moreover, this magnetic resonance scanner 14 conventionally has gradient coils (not shown) for producing gradient magnetic fields. The functioning of such a magnetic resonance scanner 14 is such that the nuclear spins, oriented in the basic magnetic field, of the atoms in the subject under examination are excited by the radiated radio-frequency pulses so that they are deflected from their equilibrium position. The nuclear spins then precess around the direction of the basic magnetic field. The magnetic resonance signals produced in this way are detected by radio-frequency receiving antennas. The receiving antennas can be either the same antennas used to radiate the radio-frequency pulses or separate receiving antennas. For spatial coding, during the detection of the magnetic resonance images the gradient coils are used to superimpose rapidly switched gradient fields on the basic magnetic field. Finally, magnetic resonance images are produced from the raw image data acquired by the receiving antennas.

The scanner 14 is controlled by a system control unit 16, here shown separately. As a user interface, here a terminal 17 is connected to the system control unit 16. Via this terminal, an operator can operate the system control unit 16 and thus the scanner 14. This terminal 17 has a display screen, a keyboard, and a pointer device for a graphic user interface, here a mouse. The terminal 17 can also be connected to the system control unit 16 to form a single unit. For example, the terminal 17 can be an integrated component of the system control unit 16, or the system control unit 16 can be a computer equipped with suitable software and hardware, to which there are connected a keyboard, a display screen, and, if necessary, a corresponding pointer device. Likewise, the system control unit 16, with the terminal 17 if warranted, can be an integrated component of magnetic resonance scanner 14.

For controlling the scanner 14, the system control unit 16 has a measurement control unit (sequence controller) 23. This measurement control unit 23 determines the time at which the scanner 14 emits radio-frequency pulses or radio-frequency pulse sequences, particularly gradient pulses or gradient pulse sequences, in order to carry out a predetermined measurement. This can take place fully automatically, for example on the basis of measurement protocols selected in advance via the terminal 17. The acquired image data BD, which at first are raw image data, are acquired in the system control unit 16 in a raw data acquisition device 24. The images can already be reconstructed from the raw image data in this raw data acquisition device 24. The measurement control unit 23 and the raw data acquisition unit 24 can be software modules realized on a programmable processor (not shown) of the system control unit 16.

In addition, the system control unit 16 has all additional standard components, for example a memory in which measurement protocols can be stored and in which acquired raw image data or reconstructed images can be stored. Such a memory also can be used to store patient data. For clarity, these additional standard components are not shown in FIG. 1.

According to the present invention, the system 15 has a fiber optic sensor 1 with which signals S can be acquired that represent the movement of the organ that is to be imaged. This fiber optic sensor 1 is composed of a light waveguide system 3 having a supply conductor $3_Z$ and a return conductor $3_R$, as well as a coupling device 2 that couples light L from the supply conductor $3_Z$ into the return conductor $3_R$. The light waveguide system 3 and/or the coupling device 2 are situated or formed in such a way that the portion of light that is coupled depends on an external force acting on fiber optic sensor 1. In the exemplary embodiment shown in FIG. 1, the coupling device 2 of fiber optic sensor 1 is situated on the thorax of body K of the patient.

Figure 2B:
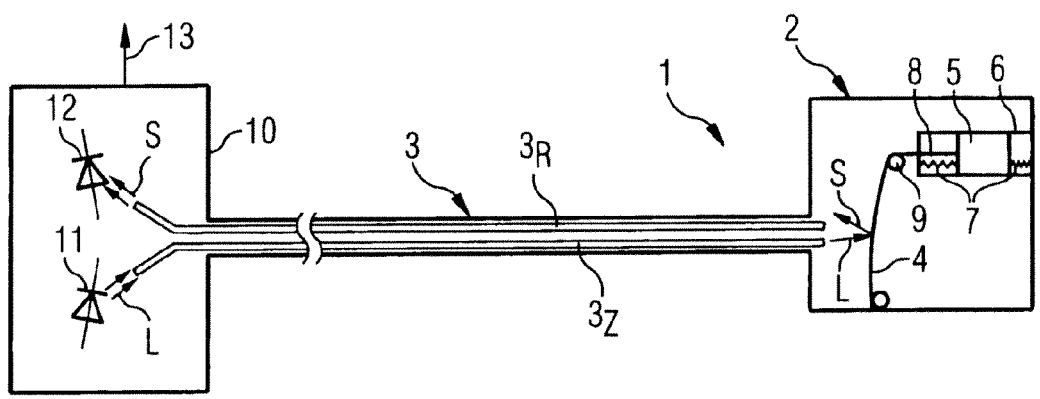
FIG. 2b shows a representation of the fiber optic sensor according to FIG. 2a, but with an external force that acts on the sensor.

The principle of operation of fiber optic sensor 1 is shown in more detail in FIGS. 2a and 2b.

As can be seen clearly in FIG. 2a, light L is conducted through the first light conductor, acting as supply conductor $3_Z$, to the coupling device 2. Here, this overcoupling device 2 has a reflector element 4 (simply called "reflector" below), for example a mirrored surface on which the light L radiated from supply conductor $3_Z$ is incident. This light L is reflected by the reflector 4 in the direction of a second light conductor, acting as the return conductor $3_R$, where it is coupled into the return conductor $3_R$. The ends of the supply conductor $3_Z$ and the return conductor $3_R$ are oriented such that when the reflector 4 is in the rest position shown in FIG. 2a, a precisely defined, preferably maximum, portion of the light L from the supply conductor $3_Z$ is reflected into the return conductor $3_R$ by reflector 4.

In the present exemplary embodiment, the reflector 4 is a reflecting flexible wall or the like that is fixed to one side of the housing of overcoupling device 2 and is coupled at another point to a joint 9 by a connecting rod 8. This connecting rod 8 is in turn coupled to a balance mass 5 held in the guide sleeve 6. The balance mass 5 is held flexibly in the guide sleeve 6 by spring elements 7. The spring elements 7 ensure that the balance mass 5 is situated in the center rest position depicted in FIG. 2a, in which the reflector 4 is a flat surface, without the action of an external force.

The spring elements 7 are small mechanical springs. In principle, however, any kind of suspension, for example a hydraulic suspension or other damping elements, can be used. What is essential is that the suspension elements be set such that balance mass 5 is deflected even in the case of small external accelerating forces, and that it returns to the depicted rest position very quickly and, as far as possible, without a large degree of overshooting. Given a correspondingly fine setting of the components of the coupling device 2, the sensor can register even small external forces, representing for example the sounds of the heart. Alternatively, the reflecting surface can be coupled to a membrane that reacts, for example, to acoustic pressure, or can itself be formed as such a membrane. Consequently, the sensor can act as a "fiber optic microphone."

Because here in the rest position the reflector 4 forms a flat surface, the ends of the supply conductor $3_Z$ and the return conductor $3_R$ must be oriented symmetrically to the reflector 4 in order to couple the maximum portion of light L into the return conductor $3_R$, because the angle of incidence (entry angle) of light L on reflector 4 corresponds to the angle of reflection (exit angle).

FIG. 2b shows the situation in which balance mass 5 has been pushed slightly out of the rest position. In this case, the flexible reflector 4 bends somewhat out of the parallel plane, so that the light L coming from the supply conductor $3_Z$ is no longer coupled precisely into the return conductor $3_R$.

The light conducted back through the return conductor $3_R$ is thus a signal S that directly represents the movement of the sensor 1 or the coupling device 2. This signal S can be appropriately evaluated.

The reflector device can be constructed differently from the manner described; for example, it could have a number of reflective surfaces. Moreover, instead of a reflector device 4, a different type of overcoupling device can be used. For example, the ends of the supply and return conductors $3_Z$, $3_R$ can be situated opposite one another, and an element can be situated between them that attenuates the light to a greater or lesser degree dependent on an external force.

For the controlling the sensor 1, here a sensor control unit 10 is used. In the exemplary embodiment, in the sensor control unit 10 a first light-emitting diode 11 produces the light L that is coupled into the supply conductor $3_Z$. Via a photodiode 12, the signal S returning from the return conductor $3_R$ is then acquired. After conversion of light signal S into an electrical signal by the photodiode 12, this electrical signal can then be arbitrarily further processed, for example digitized and converted into a different form.

A pre-processing of the signal is also conceivable, for example in order to attenuate or filter out disturbances or overshooting, etc.

In particular, it is possible that in such a sensor control unit 10 the acquired signal S, which at first represents for example a breathing movement and/or a heartbeat of the patient, can be converted into a different signal that better reproduces the movement of the organ. Possibilities for the conversion of various signals into one another can be found, for example, in the already-cited U.S. Published Application 2004/0111025.

It is also possible to process or pre-process the light signal itself, with the aid of suitable optical components.

At an output 13 of the sensor control unit 10, the desired output signal can be made available. It should be noted that as an output signal the light signal itself, or the light signal converted only into an electrical signal, can be emitted, and the further processing or pre-processing of the signal S can also take place in other components of the system 15.

The various possibilities for connecting the light-emitting diode 11 or the photodiode 12 in the sensor control unit 10 are not shown in the representations in FIG. 2a and FIG. 2b, which are merely schematic. The connections can be implemented by those skilled in the art as required.

In the exemplary embodiment shown in FIG. 1, this sensor control unit 10 is a component, realized partly in the form of hardware and partly in the form of software, of the system control unit 16. For example, the sensor control unit 10 can be constructed in the form of a sensor interface card.

In order to combine the acquired signal S with the acquired image data BD, the system 15 offers various possibilities. For example, the measurement of the raw image data can already be gated in real time, dependent on the acquired signal S. For this purpose, in the measurement control unit 23 there is a gating unit 20, here in the form of a software subcomponent, that controls the image data acquisition on the basis of signal S acquired by sensor 1.

Likewise, the system control unit 16, here realized as a software subcomponent of the raw data acquisition device 24, has a marking unit 19 that uses the signal S to correspondingly mark the recorded image data BD. For example, the image data BD can be provided with time markers that correspond to a time scale that is correlated with the signal S. However, in the depicted exemplary embodiment the marking preferably takes place in such a way that each signal value determined at a particular time during the recording of the image data BD by the fiber optic sensor 1 is stored in coded fashion in the associated image data set. These image data sets are then emitted as marked image data $BD_M$.

In the present case, as well as in the case of a software subcomponent, the measurement control unit 23 has a signal analyzing device 21 that analyzes the signal S transmitted by the sensor control unit 10 in order to determine whether anomalies occur in the movement of the organ. For this purpose, the system control unit 16 contains a memory 22 in which sample signal sequences are stored. The signal analysis device 21 has a comparator unit that compares signal sequences coming from the sensor control unit 10 with this sample signal sequence.

Inside the sensor control unit 10 shown in FIG. 1, a signal output unit 18 can be provided to ensure that signal S, or the signal sequences, acquired by sensor 1 are transmitted to the signal analysis device 21, the gating unit 20, and/or the marking unit 19 in the form required by the relevant components 18, 19, 20. Together with the signal analysis device 21, the gating unit 20, and the marking unit 19, this signal output unit 18 of sensor control device 10 forms a very convenient signal combining device for combining, in an arbitrary manner, the image data with the signal S representing the state of movement of the organ.

In the depicted exemplary embodiment, the system control unit 16 is connected to a bus 34 of a radiological information system RIS or of an image archiving and communication system (PACS: Picture Archiving and Communication System). Here, the scanner 14 forms with the system control unit 16 and the terminal 17, one of many "modalities," as they are called, within this system, which are likewise connected to bus 33.

Via the bus 34, the marked image data $BD_M$ are transmitted to other components of the RIS or PACS. Here, image data $BD_M$ can be transmitted according to the DICOM standard (Digital Imaging and Communication in Medicine), the marking (here, the associated value of the synchronously measured signal S that represents the movement of the organ) being made at a defined point in the format.

Additional components of the system connected to the bus 34 include, for example, various image reproduction devices or output devices, such as filming stations, printers, mass memory units, etc., in order to permanently archive or intermediately store images until they are viewed on an image reproduction device or are printed at a filming station or a printer.

As an additional component, here only one image reproduction device 25 is shown. This image reproduction device 25 is composed of a control computer 32 to which are connected a display device 26 having a display screen 27, as well as a keyboard and a pointer device, here again a mouse. On the display screen 27, among other things the image data produced by imaging system 15 can be presented. In addition, a speaker 28 is connected to the control computer 32.

The control computer 32 here has, preferably in the form of software components implemented on a suitable processor of control computer 32, a mark reader 29, an image output control unit 31, a selection device 30, and an audio output control unit 33. In addition, the control computer 32 has all other standard components of such a control computer of an image reproduction device, which are not shown here for clarity.

First, the marked image data $BD_M$ are supplied to the mark reader 29. This mark reader 29 is able to read the markings in the marked image data $BD_M$, and in this way to reconstruct the signal S.

The signal S is then emitted acoustically via audio output control unit 33 and the connected speaker 28. At the same time, image output control unit 31 ensures that the associated image data are synchronously displayed on display screen 27 in the form of images.

Using the keyboard and, if necessary, the mouse, it is possible for the operator to enter control and selection commands SB into the control computer 32, for example in order to set the output speed of the image data and audio signals.

Particularly on the basis of the audio signals, it is very easy for the operator to immediately recognize a deviation in the cyclical movement. In this way, a possible pathology can be quickly determined by a deviation in the heartbeat. By entering appropriate control and selection commands SB to the selection unit 30, on the basis of the sounds of the heart the operator can then select a particular time segment. The selection unit 30 thereupon controls the image output control unit 31 and the audio output control unit 33 in such a way that these units again reproduce the signal S and the associated images in synchronized fashion in the time period selected using selection device 30. Here it can also be ensured that in a cine-loop mode, heart sounds acquired within the settable time interval, and the associated image information, can be continuously repeated in an endless loop, until the operator interrupts the output.

The present invention therefore permits, without a large preparation expense, a very convenient and rapid recognition of anomalies during measurement, in particular for organs that move in cyclical fashion, such as for example during cardiac examinations. In addition, however, the method can be used for the rapid and simple investigation of non-cyclical movements, such as for example swallowing movements of the esophagus or peristaltic movements in the small intestine.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing images of a moving organ in a living subject, comprising the steps of:
   acquiring image data representing successive images of a moving organ in the living subject using an imaging modality;
   disposing a fiber optic sensor exclusively at an exterior of said subject, said fiber optic sensor having an inertial mass that is displaced by an acceleration force or sound pressure caused by movement of said moving organ, wherein said fiber optic sensor comprises:
   a light waveguide arrangement comprising a light supply conductor and a light return conductor; and
   a coupling device configured to interact exclusively with an exterior of the living subject in which the moving organ is disposed, wherein the coupling device is dependent on an external force generated by the moving organ and acting on said coupling device, and wherein the coupling device comprises a reflector disposed to reflect light from the light supply conductor into the light return conductor, and a movably mounted inertial mass mechanically connected to the reflector, the reflector reflecting a portion of light emitted from the light supply into the light return conductor dependent on a position of the inertial mass.

2. A method as claimed in claim 1 comprising electronically marking said image data for correlation with said signal.

3. A method as claimed in claim 1 comprising controlling a time of said image data acquisition using said signal.

4. A method as claimed in claim 1 comprising in said image data, using said signal to detect an occurrence of an anomaly in said movement of said moving organ, and marking image data acquired during the occurrence of said anomaly.

5. A method as claimed in claim 4 comprising detecting the occurrence of the anomaly by comparing a signal sequence in said signal with a sample signal sequence.

6. A method as claimed in claim 5 wherein said movement of said moving organ is cyclical, and comprising obtaining said sample signal sequence in a cycle of said movement preceding the cycle containing the occurrence of the anomaly.

7. A method as claimed in claim 1 comprising using said signal, detecting an occurrence of an anomaly in the movement of said moving organ, and starting acquisition of said image data depending on the occurrence of the anomaly.

8. A method as claimed in claim 7 comprising detecting the occurrence of the anomaly by comparing a signal sequence in said signal with a sample signal sequence.

9. A method as claimed in claim 8 wherein said movement of said moving organ is cyclical, and comprising obtaining said sample signal sequence in a cycle of said movement preceding the cycle containing the occurrence of the anomaly.

10. A fiber optic sensor for acquiring a signal representing movement of an internal moving organ in a living subject, comprising:
   a light waveguide arrangement comprising a light supply conductor and a light return conductor;
   a coupling device disposed relative to said light supply conductor and said light return conductor to couple light from said light supply conductor into said return conductor, said coupling device being configured to interact exclusively with an exterior of the living subject in which the moving organ is disposed, and said coupling device coupling said light is dependent on an external force generated by said moving organ and acting on said coupling device; and
   said coupling device comprising a reflector disposed to reflect light from said light supply conductor into said light return conductor and a movably mounted inertial mass mechanically connected to said reflector, said reflector reflecting a portion of light emitted from said light supply conductor into said light return conductor dependent on a position of said inertial mass.

11. A fiber optic sensor as claimed in claim 10 wherein said coupling device comprises a membrane connected to said reflector, said membrane being responsive to acoustic pressure and causing a portion of light emitted from said light supply conductor to be reflected by said reflector into said light return conductor dependent on acoustic pressure acting on said membrane.

12. A system for producing a time-limited image of a moving organ in a living subject, comprising:

an imaging modality adapted to interact with a living subject to acquire image data of a moving organ in the subject;

a fiber optic sensor comprising a light waveguide arrangement comprising a light supply conductor and a light return conductor, a coupling device disposed relative to said light supply conductor and said light return conductor to couple light from said light supply conductor into said return conductor, said coupling device being configured to interact exclusively with an exterior of the living subject in which the moving organ is disposed, and said coupling device coupling said light dependent on an external force generated by said moving organ and acting on said coupling device, and said coupling device comprising a reflector disposed to reflect light from said light supply conductor into said light return conductor and a movably mounted inertial mass mechanically connected to said reflector, said reflector reflecting a portion of light emitted from said light supply conductor into said light return conductor dependent on a position of said inertial mass; and a computerized control arrangement connected to said fiber optic sensor and to said imaging modality that controls operation of said imaging modality to correlate acquisition of said image data with said signal, to obtain a time-limited image of said moving organ.

13. A system as claimed in claim 12 wherein said computerized control arrangement comprises a marking unit electronically marks said image data for correlation with said signal.

14. A system as claimed in claim 12 wherein said computerized control arrangement controls a time of said image data acquisition using said signal.

15. A system as claimed in claim 12 wherein said computerized control arrangement comprises an analysis unit that, using said signal, detects an occurrence of an anomaly in the movement of said moving organ, and starts acquisition of said image data depending on the occurrence of the anomaly.

16. A system as claimed in claim 15 wherein said analysis unit compares a signal sequence acquired by the sensor with a sample signal sequence.

* * * * *